(12) United States Patent
Thompson et al.

(10) Patent No.: US 10,610,131 B1
(45) Date of Patent: Apr. 7, 2020

(54) MOBILE EQUINE LIMB INERTIAL SENSING SYSTEMS AND METHODS

(71) Applicant: Cadence Dynamics, LLC, Loveland, CO (US)

(72) Inventors: John D. Thompson, Loveland, CO (US); Leah Estberg, Loveland, CO (US)

(73) Assignee: Cadence Dynamics, Inc., Loveland, CO (US)

( * ) Notice: Subject to any disclaimer, the term of this patent is extended or adjusted under 35 U.S.C. 154(b) by 894 days.

(21) Appl. No.: 14/705,251

(22) Filed: May 6, 2015

Related U.S. Application Data (60) Provisional application No. 61/989,368, filed on May 6, 2014.

(51) Int. Cl.
*A61B 5/11* (2006.01)
*A61B 5/00* (2006.01)

(52) U.S. Cl.
CPC ............ *A61B 5/112* (2013.01); *A61B 5/6828* (2013.01); *A61B 2503/40* (2013.01); *A61B 2562/0219* (2013.01)

(58) Field of Classification Search
CPC ...................................................... A61B 5/112
See application file for complete search history.

(56) References Cited

U.S. PATENT DOCUMENTS

| | | | |
|---|---|---|---|
| 4,774,679 A | * | 9/1988 | Carlin .................. A61B 5/0002 273/454 |
| 7,601,126 B2 | | 10/2009 | Keegan et al. |
| 7,673,587 B2 | | 3/2010 | Davies |
| 8,715,208 B2 | | 5/2014 | Hodgins et al. |
| 2007/0000216 A1 | | 1/2007 | Kater et al. |

(Continued)

OTHER PUBLICATIONS

Olsen, et al "Accuracy and Precision of Equine Gait Event Detection during Walking with Limb and Trunk Mounted Inertial Sensors" Jun. 12, 2012 SENSORS, www.mdpi.com/journal/sensors 12 pages.

(Continued)

*Primary Examiner* — Charles A Marmor, II
*Assistant Examiner* — Yasmeen S Warsi
(74) *Attorney, Agent, or Firm* — Santangelo Law Offices, P.C.

(57) ABSTRACT

Embodiments of the present invention may provide a limb motion sensor system (100) used to objectively assist detection of equine lameness and even monitor change in gait quality over time. Biosensors (102) may be attached to the pair of front and/or hind limbs. Each conformally shaped biosensor device may be placed lateral to the metacarpal/metatarsal bone (e.g., attached to the lower limb). Inertial data may be collected by the set of sensor devices and may be wirelessly transferred to a portable, perhaps wearable, mobile controller and analytics unit (104) (e.g., smart phone, tablet, or the like). A signal processor application (108) may automatically segment each stride into phases and perform analyses to quantify limb motion metrics and uniformity over time for a single limb (unilateral consistency) or between the contralateral limbs (bilateral symmetry). Three-dimensional motion metrics may be processed, displayed, stored on, and even transmitted from the mobile information system.

11 Claims, 6 Drawing Sheets

(56) References Cited

U.S. PATENT DOCUMENTS

2007/0130893 A1* 6/2007 Davies ................ A01K 11/008
                                                    54/1
2011/0218463 A1* 9/2011 Hodgins ................ A61B 5/112
                                                    600/595

OTHER PUBLICATIONS

Olsen et al "Functional limits of agreement applied as a novel method comparison tool for accuracy and precision of inertial measurement unit derived displacement of the distal limb in horses" Jun. 4, 2013. Journal of Biomechanics. 6 pages.

* cited by examiner

MOBILE EQUINE LIMB INERTIAL SENSING SYSTEMS AND METHODS

PRIORITY CLAIM

This application is a United States nonprovisional utility application claiming priority to and the benefit of U.S. Provisional Application No. 61/989,368 filed May 6, 2014, hereby incorporated by reference herein in its entirety.

BACKGROUND

Mild lameness in horses is difficult to detect and monitor for changes using standard subjective evaluation methods such as visual observation of the horse in motion. The purpose of visual and riding-based lameness evaluations is to detect abnormal, asymmetric gait patterns. Biosensing technology could be used to both objectively measure asymmetric gait patterns and monitor a change in gait suggestive of lameness. These types of sensing instruments should be reliable (e.g., characterized by accuracy, repeatability, sensitivity, specificity, or the like) and easily applicable by both horse owners and veterinarians.

The main output from two commercially available lameness detection devices may be derived from two motion sensors such as discussed in U.S. Pat. No. 7,601,126 to Keegan et al and GaitCheck™ at www.gaitcheck.com, each hereby incorporated by reference herein. One sensor may be placed on top of either the head or withers and the second may be placed over the pelvis. The Keegan reference may measure vertical, 1-dimensional acceleration patterns of the head and pelvis. The motion data may be decomposed and simulated with a phase-shift equation (e.g., difference between first and second harmonics). Lameness location (e.g., limb source) and severity may be determined based on maximum and minimum positions of the head and pelvis as compared to reference (e.g. phase-shift) patterns collected from other horses. The measurement of head and torso motion may provide for an indirect assessment of normal gait and lameness limb motion patterns. Additionally, interference with the horse's natural head motion may occur when horse handlers pull on the lead rope during the gait evaluation session in order to slow an eager horse or to turn them on a circle during lunging.

Another type of biosensor system, as discussed in U.S. Pat. No. 7,673,587 to Davies, hereby incorporated by reference herein, may be designed to measure the motion of any body part of a human or animal. The system may have been designed for a wide variety of applications including avoiding injury and improvement in conditioning of equine athletes, in addition to monitoring the technique of horseback riders. The system may provide attachment of inertial sensors to various locations, such as limb segments or the torso of animals. The system may analyze all gaits (including walking, trotting, cantering, and/or galloping) under various trajectories experienced during riding (such as performing sharp turns and/or jumping over obstacles). However, the all-encompassing approach to the system may hamper sensitivity and repeatability in detecting and monitoring subtle lameness. As the devices were not designed to be mounted to specific locations, secure attachment and proper orientation may be problematic. A high volume of data collected can also lead to spurious correlations that may be an artifact of the data and neither biologically nor clinically insightful.

Non-uniformity in lower leg motion may provide sensitive lameness indicators, especially for subclinical lameness cases. Gait kinematics involves the study of inertial metrics that may characterize limb segment motion as the leg cycles through a stride. This limb motion is clinically relevant if used to detect abnormal gait patterns symptomatic of lameness as well as monitor the progress of mitigating treatments. Each stride is a full cycle of limb motion, perhaps including stance and swing phases. The stance phase (e.g. limb retraction backward) may start when the hoof impacts the ground and end upon completion of the break-over event. The break-over event may begin when the heel lifts off the ground, continue as the hoof rotates, and end as the toe lifts off the ground. The swing phase (e.g., limb protraction forward) may start with the toe lifting off the ground and end with the leg descending towards the ground just prior to impact.

Biosensors attached to horse's limbs should not only be able to sustain high acceleration and vibration, but the sensors should be tuned to measure both high and low signal ranges and frequencies adequately. This may be necessary for gaining a full understanding of equine limb inertia patterns, but may also present challenges with separating true signals from spurious signals (e.g. vibrations due to poor coupling and the like), along with interpreting signal data. A common approach to overcome these challenges may be to filter the signals. When filtering is applied, the signal amplitudes and phase are affected in such a way that analytic power may be diminished and the magnitudes may only be used for relative comparisons, rather than indicating exact absolute signal values, such as discussed in U.S. Pat. No. 8,715,208 to Hodgins, hereby incorporated by reference herein. Filtering may lead to abstracting the data away from the true signal and imposing bias in the amplitude and phase of the raw signal. The degree of filtering applied should take into consideration the objective of the signal processing. The impact of losing data from filtering should be weighed against the ability to summarize signals in a manner that makes it easier to detect common patterns.

One type of inertial measurement device such as discussed in Olsen et. al., 2013 and Olsen et. al., 2012, each hereby incorporated by reference herein, may have been designed for application to the lower limb for the main purpose of evaluating neurologic disorders in horses at the walking gait. The walk instead of the trot may be considered, and the scope of the system does not include lameness evaluation. Data collected at 200 Hz with this system undergoes the application of both low pass Butterworth filtering and wavelet symlets decomposition filters, which may obfuscate subtle gait abnormalities as discussed previously. Additionally, the relatively low sampling rate (i.e. 200 Hz) may lead to missing rapidly changing signals with higher frequency content (e.g. during impact and breakover or the like).

Another type of device was designed for attachment of the sensors to each hoof as discussed in U.S. Pat. Pub. No. US2007/0000216 to Kater et al, hereby incorporated by reference herein. The type of sensors used on this device (e.g. piezoelectric accelerometer) have limited low frequency response, rendering them insensitive to accurate measurement of limb motions during swing and weight bearing phases which are predominated by slowly changing signals. Measurement of motion throughout the stride that is sensitive to high frequency as well as low frequency signals may be helpful for accurate extraction of stride angular and displacement metrics.

The "temporal limb phasing" output as mentioned in the Hodgins reference may focus on the relative limb timing events and motion waveforms (e.g. a high level abstraction)

correlated across two limbs. Phasing differences across multiple strides are graphed as linear plots, without segmentation to separate strides or summarize motion findings from each leg. It may be useful to provide summary quantified metrics that are easier to conceptualize, as they may relate directly to segmented limb motion (e.g. stance and/or swing) as understood by veterinarians and horse owners.

In addition to providing meaningful insight into the presence and location (e.g. limb affected) of lameness, ease of use under field conditions may be important. Some systems require attachment of the devices to the horse or their tack (e.g., halter) with tape, perhaps in the Keegan and GaitCheck™ references. This can present a problem if the halter is loose or the coat isn't properly cleaned prior to attachment (perhaps resulting in the presence of dirt, loose hair, oil, or the like), as close coupling of the device to the horse may be significant to measurement accuracy and repeatability. Additionally, operation under varying temperature ranges is necessary for field use. It may be difficult to complete the calibration as needed to prevent synchronization drift for devices exposed to changing temperatures as perhaps in the Hodgins references.

Repeatability and accuracy are greatly improved if the devices are securely attached to the horse's legs. Attachment of devices to horse limbs presents unique challenges. The device should be as small and light as possible and designed to both conform to the limb and not interfere with normal locomotion. Device form factor and a secure method of attachment may better ensure device-to-horse coupling which may minimize spurious oscillatory motion resulting in improved signal integrity. The shape, size & weight (e.g., form factor) of the devices and limb attachment methods described in past systems do not appear to be well suited for sustaining relatively high equine limb acceleration, vibration, impact forces, or the like. The signals resulting from these spurious vibrations become convolved with the true signal and require filtering for their removal. A limitation of this filtering is that it may corrupt the original signal in both amplitude and phase to varying degrees throughout the stride dependent on frequency content. Maximizing device to horse coupling and thereby minimizing vibration induced artifacts may be the most effective method of mitigating this limitation of the filtering process.

Signal data processing may be required prior to data analysis and even delivery of informative gait uniformity metrics. The computer equipment often needed to perform inertial signal processing and analysis may present a challenge for convenient operation in the field, perhaps under time and mobility constraints. The horse handler should ideally be able to carry the equipment in their pocket or a portable holster, perhaps with minimal manual equipment operation requirements, even while either riding or running with horse in-hand. Additionally, decisions should be made quickly regarding selection of appropriate diagnostic procedures during a lameness exam. A significant degree of automation may be required to efficiently process multiple signal streams into a paired-limb set, divide each stride into phases, and derive meaningful limb motion metrics. Fully automated features that support the ability to recognize and exclude signal artifacts (e.g. tripping, forging, change in gait, or the like) are desirable for producing repeatable, reliable and accurate motion metrics near real-time.

The biosensor system of the Davies reference may monitor rider and horse motion and may include a data transfer (e.g., communication hub) attached to the horse. The hub can receive, store and even transmit the sensor data to a computing subsystem. This additional computing subsystem, necessary to analyze and report the data, could be difficult to carry and operate under field conditions and may add to overall system complexity. The limb motion biosensor systems described in the Hodgins and Olsen references may also require computer transport and operation in the field for data processing and analysis.

Therefore, it is desirable to provide an inertial biosensing instrument designed to alert horse owners of potential lameness and inform lameness diagnosis by equine veterinarians that can provide objective, quantified evidence of lameness location, severity and type. This device can serve as a complementary tool for the assessment of subtle gait alterations which may deliver accurate, meaningful results and may be convenient to operate (e.g., mobile and automated) under demanding field conditions.

SUMMARY OF THE INVENTION

In accordance with embodiments of the present invention, systems and methods may be used to measure and analyze three-dimensional equine limb motion. A conformally shaped biosensor device, perhaps contained within a casing, may be attached to the lower leg, perhaps by a fastener, in a manner that may facilitate device-to-horse coupling, perhaps minimizing difficult to filter vibrations, especially during high impact forces that occur when the hoof lands on the ground and just prior to leaving the ground during breakover. Such a device may also be substantially lightweight, perhaps achieving minimization of vibrations by minimizing any inertia not associated specifically with equine strides. Automated analysis tools specifically designed to extract the three-dimensional motion metrics of the lower limb may be sensitive for detection and characterization of changes or abnormalities in gait. The system may be capable of collecting, segmenting, and processing lower limb motion stride data in a manner useful for nonuniformity detection, localization, and monitoring. Raw three-dimensional angular limb velocity may be transformed into various metrics that provide meaningful and easily visualized insight into lameness and gait quality (e.g. lower limb angular range of motions, angular velocities, other derivative metrics, or the like).

Embodiments of the present invention may provide a signal processor software application which may display limb motion uniformity of use for determination of abnormal gait patterns. Ease of use and cost savings may be provided by offering the data analysis and reporting module on portable, perhaps widely available mobile devices (e.g., smart phones, tablets, or the like) and software (e.g. spreadsheets, or the like), perhaps already in use for various other purposes. This may allow a single person to operate the system, perhaps while leading or even riding the horse, and may offer immediate feedback (e.g., audio notification when automated stride data collection has been started and completed). Objective measurement of limb motion metrics can be used for identifying the limb, or limbs, affected and even characterizing lameness type, severity, and progression over time. Additionally, the horse may serve as their own reference by comparing the motion uniformity over time for a single limb (consistency) or between the left and right, front and/or hind contralateral limb pairs (symmetry). The various reported limb motion metrics (e.g. lower limb angular range of motions, stride phase durations, or the like) and uniformity metrics may be easy to conceptualize because they may relate directly to the actual limb motion as understood by veterinarians and horse owners. Additionally, this measurement device could be applied to humans and other animals or the like.

DETAILED DESCRIPTION OF THE PREFERRED EMBODIMENTS

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 1:
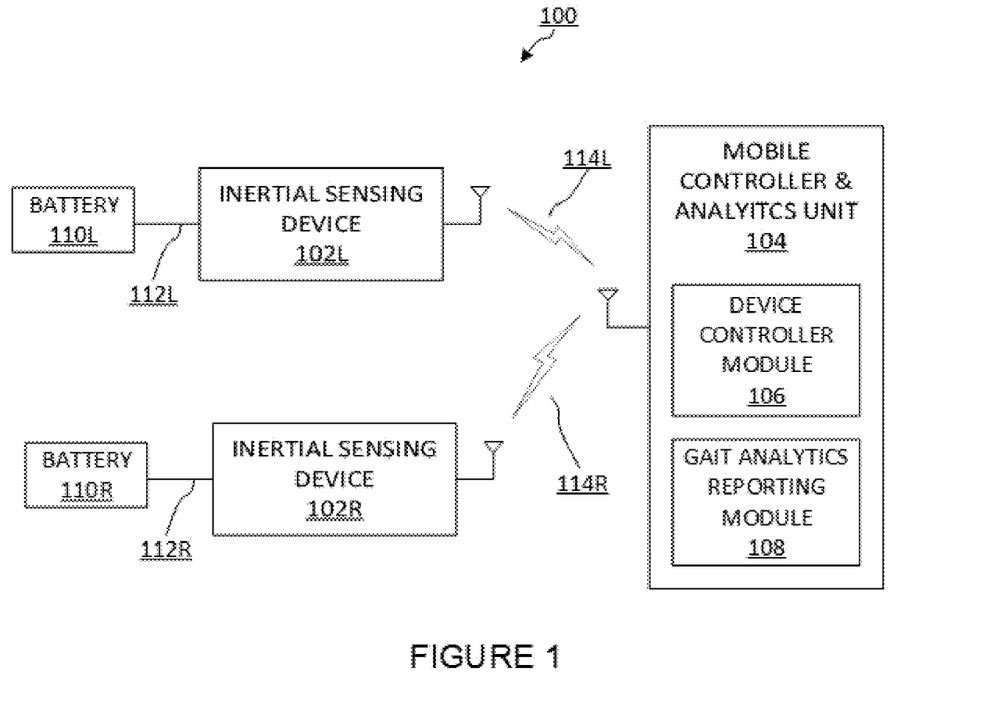
FIG. 1 shows a block diagram of the inertial sensing system in accordance with various embodiments of the present invention.
Figure 2:
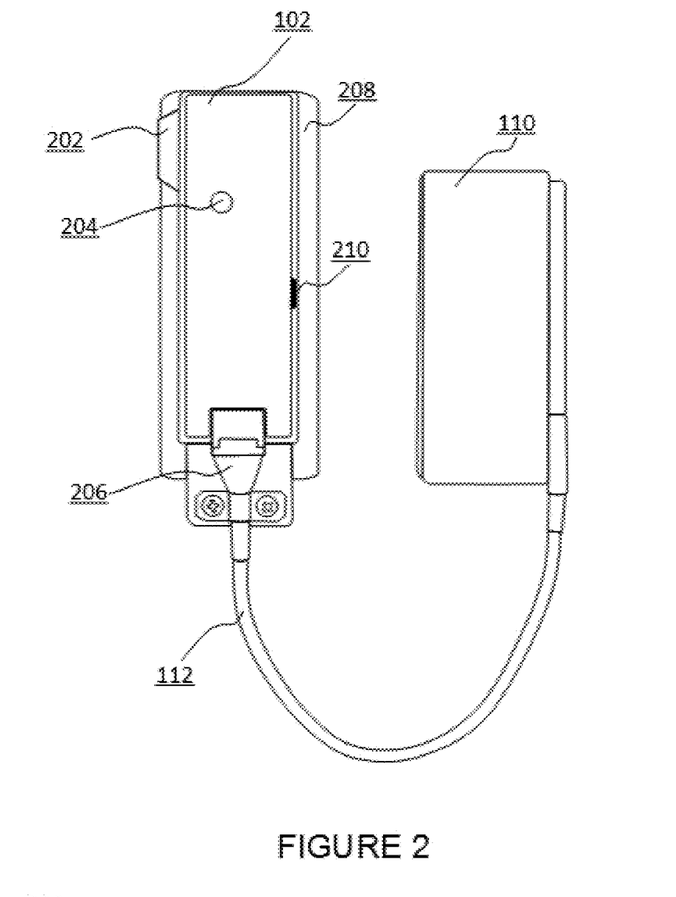
FIG. 2 shows a schematic diagram of the front perspective view of the inertial sensing device, battery and connecting wire in accordance with various embodiments of the present invention.
Figure 3:
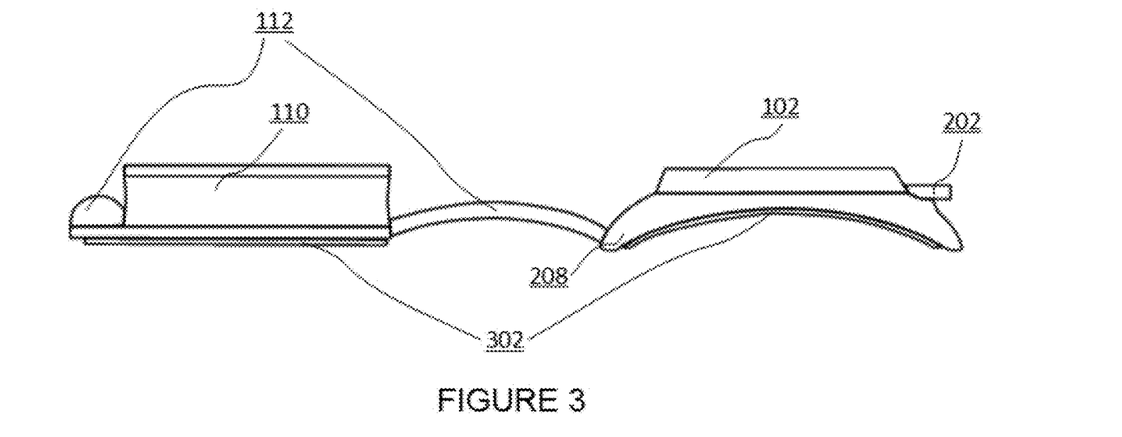
FIG. 3 shows a schematic diagram of the top view of the inertial sensing device, battery and connecting wire in accordance with various embodiments of the present invention.

FIG. 1 illustrates an example of an equine limb inertial sensing system 100 according to embodiments of the present invention. A pair of inertial sensing devices 102 (left L and right R) may be located on the lower limb segment that may include the third metacarpal and/or metatarsal bone, perhaps depending on whether either one or both of the front or hind limb pairs are evaluated. The biosensor devices may include casings and inertial sensors, such as gyroscopes or the like, perhaps for measuring the three-dimensional motion of the lower limb. Each sensing device may be powered by a battery 110 which may be attached by wiring 112. FIGS. 2 and 3 provide detailed example views according to embodiments of the present invention. The biosensor device may be housed separately from its battery power supply, perhaps to minimize size and weight, improving device-to-horse mechanical coupling and reducing unnecessary vibration. This separation of the device from the battery may extend device longevity, allowing replacement of the battery as needed without replacing the biosensor device via detachment of the wiring connector 206. The device may include an indicator 204 for displaying the power status (e.g., on/off), battery remaining charge status, battery charging status, wireless connection status, operation errors, and the like. The device may also provide options to power the device on or off (e.g. reed switch, mechanical switch, or the like), a wireless antenna 202, and perhaps even options to supply battery charge by applying external power through a charging port 210 (e.g. using readily available USB chargers or computer USB ports). The inertial sensing device may be designed to collect specific types of stride data (e.g., walk, trot, or the like) perhaps for measurement of limb motion uniformity. The design may include a limb conformal interface 208 and a directly applied hook fastener or the like 302 (e.g., a Velcro® hook strip) which may facilitate device-to-horse coupling, perhaps minimizing unnecessary vibration, especially during high impact forces that occur when the hoof lands on the ground and just prior to leaving the ground during breakover. The design may include a highly affixed equine motion detector, perhaps so highly affixed as to be directly responsive to equine bone motion. Such a highly affixed device may, when attached, have substantially no material, such as compressible foam or the like, between it and the horse's limb. So long as the shape of the detector is conformal, attachment may be achieved in a wide variety of ways without losing the great advantage of secure, conformal coupling. To facilitate inertial minimization, the device may weigh approximately 30 grams.

As shown in FIG. 1, a portable controller and analytics unit 104 may be used to wirelessly collect gait data from each device pair using the device controller module 106 in addition to analyzing the data into limb motion metrics, perhaps using the gait analytics reporting module 108. The device controller module 106 may interface wirelessly 114 with each pair of inertial sensing devices 102 (e.g., left and right), perhaps for the purpose of initiating and even halting gait evaluation sessions, performing multiple data collection runs for each session, decrypting/encrypting and storing of collected data, monitoring device status (e.g. battery charge level, temperature, and/or wireless communication integrity), and even for remotely powering down the devices. The device controller module 106 may perform many of the low level operations such as, but not limited to, interface with the mobile controller unit 104 embedded wireless hardware and even prepare the raw data collected from the devices 102 for use by the gait analytics reporting module 108. The mobile controller unit 104 may be operated in close proximity to the inertial sensing devices 102, perhaps to reduce the risk of data loss which may be due to wireless signal integrity, and even extend device use time before the battery requires recharging. Therefore, the controller unit 104 may be a portable device such as, but not limited to, a smart phone or tablet or the like that may be carried on the handler's person while leading or riding the horse, or perhaps by securing to the horse directly (e.g., attached to the saddle, surcingle, or the like). Ease of use and cost savings may be provided by offering the controller unit 104 as a portable, widely available mobile device that can run software, perhaps with touch screen capability, which may already be in use for various other purposes. This may also provide the options for a single person to operate the system, perhaps while leading or riding the horse, and may offer immediate feedback (e.g., audio notification that stride data collection has started and has either been interrupted or successfully completed, or the like).

The gait analytics reporting module 108 may be a software application designed to automatically segment strides from a continuous run, divide each stride into phases (e.g., landing, weight-bearing, breakover, swing, or the like), and perhaps even translate inertial metrics (e.g., three-dimensional lower limb angular velocity) into useable limb motion metrics (e.g., angle of the swing of the metatarsal bone between full protraction and retraction or the like). The quantified output from this module may support alerting the horse owner to non-uniform gait patterns indicative of reduced athletic performance or lameness, and perhaps even the veterinarian performing an evidence-based lameness evaluation or monitoring healing progress. The gait analytics reporting module 108 may either operate on the mobile unit 104 or perhaps on stride data downloaded (wirelessly, USB wire connection, or the like) to a personal computer. The data analysis tools used in this segmentation may have applications beyond the equine realm, including, as but a few examples, the ability to segment relatively high acceleration events, relatively high deceleration events, upward motion events, downward motion events, forward motion events, transitory motion events, sequential motion events, and sequential transitory motion events.

Figure 4:
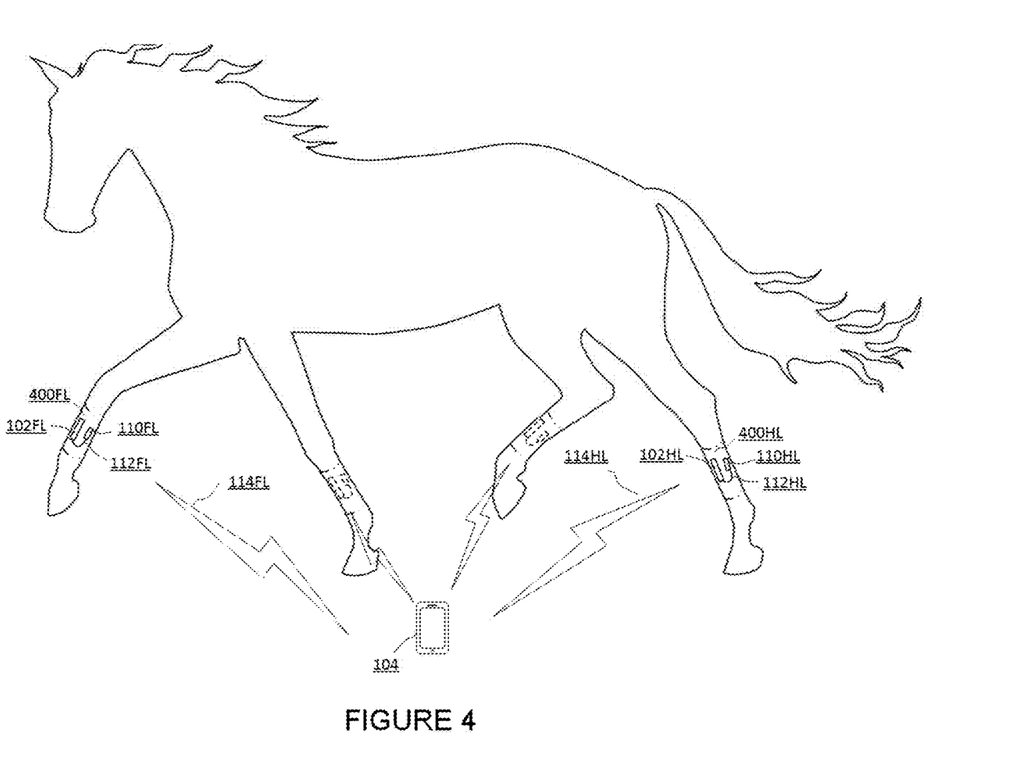
FIG. 4 shows a schematic diagram of the sensor device pairs which can be attached to either or both front (F) and hind (H) limb pairs (L=left) in accordance with various embodiments of the present invention.

FIG. 4 illustrates an example of the manner of placing the inertial sensing devices on the lateral side (outside) of the front and hind pairs of limbs according to embodiments of the present invention. A set of sensing devices 102 and batteries 110 may be attached to the lateral aspect (e.g., outside) of leg wraps 400 which may be applied to the limbs (e.g., front left (FL) and right (FR); and hind left (HL) and right (HR) or any combination thereof; the right lateral aspect is not directly visible). The biosensor device form may be light-weight, enclosed (e.g. weather-, water-, dust-proof or the like), slim (distance outward from the leg), and may conform to the natural shape of the leg 208 to facilitate device-to-horse coupling. The device may be located directly over firm, boney areas (e.g., perhaps the third metacarpal or even metatarsal bone), perhaps with minimal motion due to tightening, relaxation, and even vibration of soft tissue structures (e.g., skin, ligament, tendon, and/or muscle) during each stride cycle. Additionally, the device and battery may be securely applied with a hook fastener or the like 302 (e.g., with a Velcro® hook strip) perhaps to a slim, elastic wrap made of loop fabric that can be tightly applied to the leg 400. Unnecessary vibration may be minimized by a light-weight, slim device, perhaps applied in a secure, conforming manner to a boney area of the leg. Attachment of the device and battery to the leg wrap with a hook fastener allows convenient replacement or washing of the wrap pair as needed.

Figure 5:
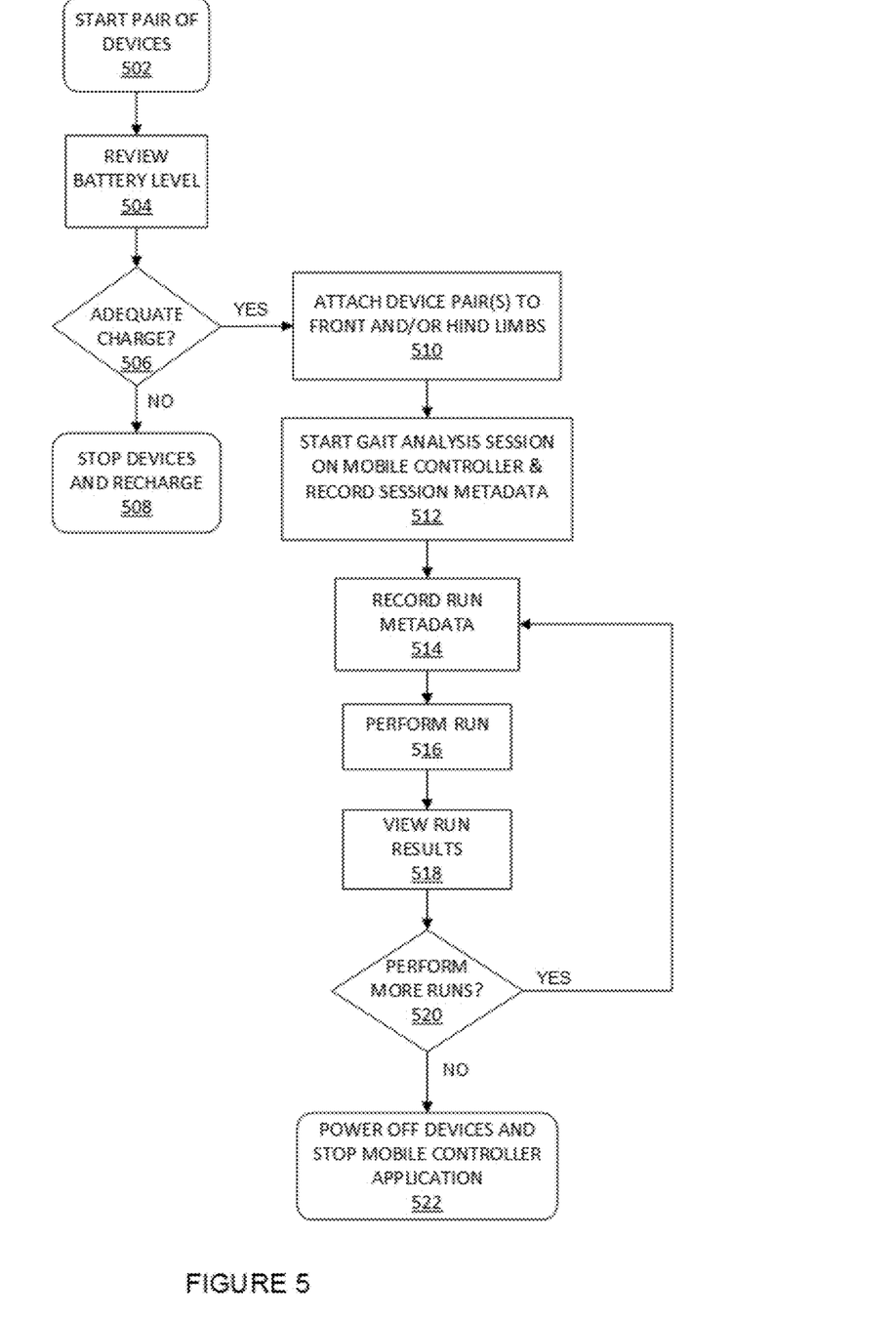
FIG. 5 shows a flow chart illustrating a device application and controller unit usage method in accordance with various embodiments of the present invention.

FIG. 5 illustrates an example of the manner in which to apply the pair(s) of inertial sensor devices 102 and even the summary description of operating the controller and analytics unit 104, perhaps used to collect and process the inertial data. The device 102 and even the mobile controller and analytics unit 104 user interfaces may be used to perform the following described operations.

Once ready to prepare for a gait analysis session, the user can start 502 the set of inertial sensing devices (102), perhaps by turning them on directly (e.g. not remotely through the controller and analytics unit 104). The user may review the battery (110) charge level 504-506 to ensure charge is adequate for the data collection session. If the charge is not adequate, they can choose to stop and recharge 508 the battery. If the charge is adequate, the devices may be attached 510 to the pair of front and/or hind limbs with leg wraps (400) or the like.

When ready to start performing the gait analysis session, the user can start 512 the mobile device controller (104) and even record session metadata such as horse identifying information, leg pair evaluated (e.g., front or hind), device pair identifier (e.g., serial number), and even the footing conditions over which the runs may be performed (e.g., firm dirt, grass, gravel, or the like). Additionally, for each run performed, the various conditions that may influence the results can also be captured as run metadata 514 (e.g., joint flexion, local anesthetic injection, therapeutic shoeing, miscellaneous notes, or the like). It may also be possible to capture photographs (e.g., healing limb wounds or the like) and video recordings of the horse in motion (e.g., trotting or the like) as run-specific metadata 514 that can be sent to a veterinarian for follow-up evaluation in addition to the gait analysis results. This session and run specific metadata can be captured using touch screen enabled selection controls (e.g., using pre-defined dropdowns, checkboxes, or the like), typing text or utilizing voice recognition to convert audio into text, recording verbal notes as audio recordings, and even taking either photos or video, or the like. This structured metadata collected (including run date and time captured from the mobile device) can be stored with the gait data and used to identify the horse along with the conditions for each run as needed for proper interpretation of the gait findings. When performing a run event, the horse can be ridden or hand-led to travel at a symmetric gait (e.g., walk, trot, fox trot, or the like) with the intent to collect a reasonable number of valid strides to support statistical testing, perhaps at a consistent speed 516. As the run is performed, the device controller module (106) can collect the trot stride inertial metric data and the gait analytics reporting module (108) may carry out the analysis and reporting. Once completed, the user may view the limb motion uniformity metrics 518. The option may also be provided for transmitting the raw stride inertial data for the purpose of further analysis. Minimization of spurious motion can allow the raw equine data to be useful. The data may be useful while remaining substantially unfiltered, thereby possibly allowing for data relative to nonspurious motion to remain integral for analysis. Transmission of the information for further evaluation or review can be performed using the mobile device controller (104) which can send the information electronically (e.g., email, electronic communications, or the like) or from data downloaded to a personal computer.

After reviewing results, the user may choose to delete the run and/or perform another run event 520, as multiple run events may be included in a data collection session. Once the session is completed, the inertial sensing devices (102) can be powered off directly at the devices themselves or even remotely by the device controller module (106) application, which in turn can then be stopped 522, terminating the session automatically.

Figure 6:
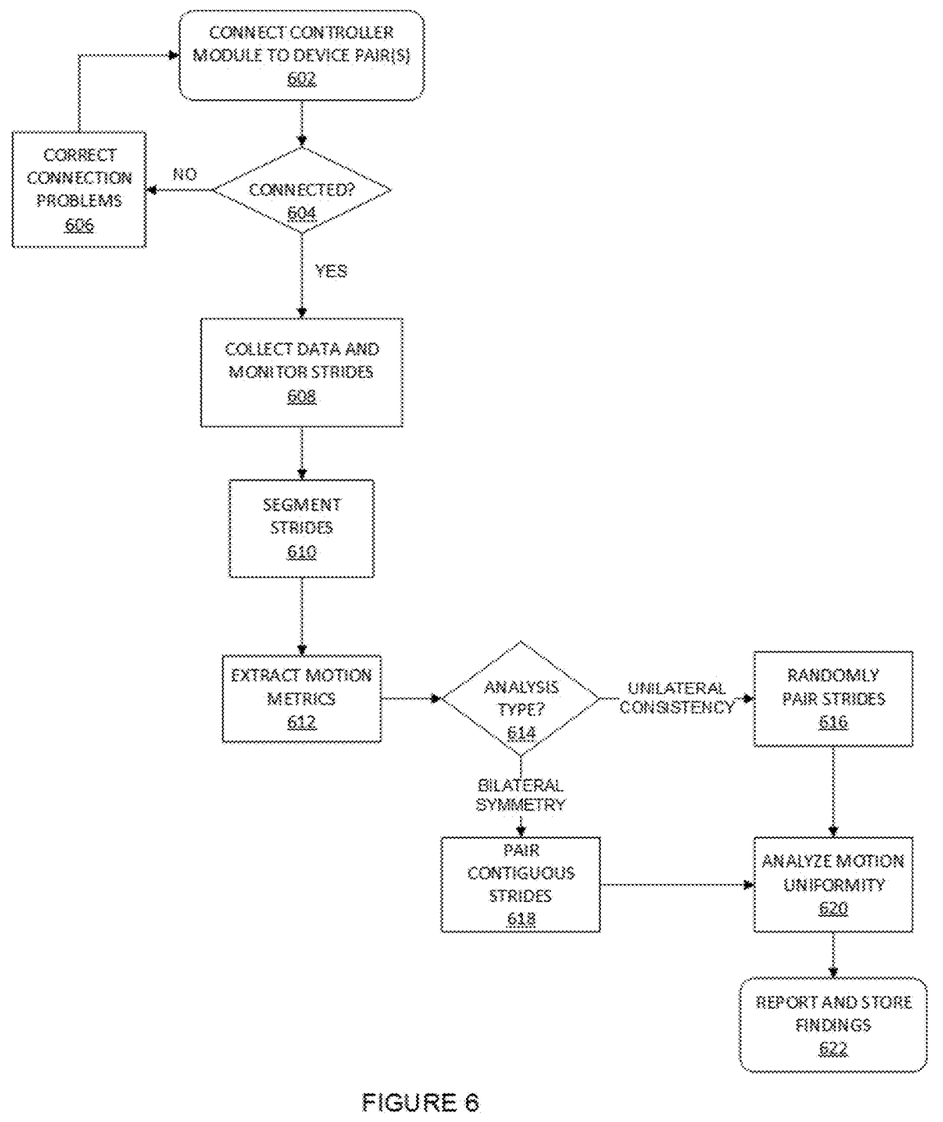
FIG. 6 shows a flow chart illustrating a data analysis method in accordance with various embodiments of the present invention.

FIG. 6 illustrates an example of a manner in which to complete data collection, analysis, and even reporting, perhaps using the mobile controller and analytics unit 104.

These activities may represent the details for two summary 'perform run' and perhaps even 'view run results' tasks described previously in the example of FIGS. 5 (516 and 518). First, when the user may choose to establish a connection 602, the device controller module (106) can initiate wireless connection (114) to the set of devices 102. Connection problems 604 may need to be corrected 606 before data collection can begin (e.g., moving the controller within communication range of devices, ensuring the devices have not timed out and automatically shut off to conserve battery charge as might occur during a lengthy therapy, exercise warm-up session, or the like). Upon successful connection, the data collection for a run may automatically commence 608, perhaps by the controller module (106), once a valid stride has been detected from each device (102). This may provide a dynamic lag period as may be needed to allow the operator to store the mobile unit (e.g., in their pocket or holster, or the like), position the horse, and/or perhaps even complete a joint stress flexion prior to the run. The operator may also specify a timed lag period (e.g., to complete a joint flexion or the like) that may end with an audible notification, perhaps prior to the run data collection commencing. As the data may be collected, the controller module (106) may also perform preliminary monitoring for valid trot strides, perhaps in order to provide feedback to the horse handler during operation. Once the run is completed, the controller module (106) may automatically end data collection based on determination of lack of strides (e.g. the horse is stationary) and may disconnect from the devices (102) (perhaps to conserve battery power). The operator may choose to manually end the controller module (106) data collection and disconnection from the devices (102). The gait analytics and perhaps even the reporting module (108) may access the data collected in order to perform and report the analysis as well as store the results. Optionally, the operator may delete run data collected along with the analysis results.

Figure 7:
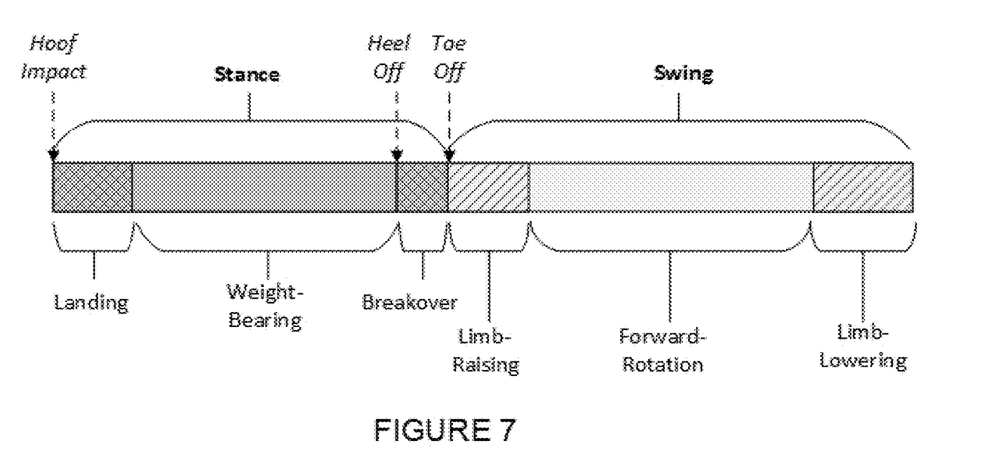
FIG. 7 shows a schematic diagram of stride phases (stance, swing), subphases (e.g. stance landing, weight-bearing and breakover), and stride events (hoof impact, heel off, toe off), in accordance with various embodiments of the present invention.

The analytics and reporting module (108) may automatically segment the run into strides and may divide each stride into phases and sub-phases 610 perhaps based on detection of stride events and limb motion signature patterns (e.g., see FIG. 7 for an example illustration of a non-limiting sampling of types of stride phases, stride events, and sub-phases or the like). For example, the hoof impact event may be detected and may be used to determine the beginning of the landing sub-phase of stance. As the limb motion may stabilize following impact, the landing ends and even the weight-bearing sub-phase may begin. The hoof heel off event may be used to end weight-bearing and may begin the breakover sub-phase. The hoof toe off event may be used to end the breakover sub-phase and may begin the swing phase, perhaps occurring as the leg may be raised. The swing phase may be subdivided in a similar manner into limb-raising, forward-rotation, and even limb-lowering sub-phases, perhaps based on limb motion patterns. During stride phase segmentation, the final validation for usable strides may also occur. Divergent strides can be identified through, but not limited to, detection of indistinguishable stride phase markers, known as stride phase aberration patterns, and even unexpected stride phase durations. Once the invalid strides (e.g., change in gait, tripping, slipping, forging, turning, or the like) may be detected and even excluded, the usable stride 610 inertial sensor outputs (e.g., three-dimensional angular velocity roll, pitch and yaw components or the like) may be processed, perhaps to extract limb inertial motion metrics and even stride phase duration metrics 612. In order to minimize loss of information, signal filtering may be omitted. The roll, pitch and yaw angular displacements over each stride phase may be determined by integrating the raw sensor angular velocities over the time interval determined by the start and end of each phase. These displacements may then be rotated from the device's frame into the earth frame, perhaps using standard 3D rotation matrices to determine the limb protraction-retraction (forward-back), adduction-abduction (sideways inward-outward), and even rotational (twisting) angular displacements for each stride phase. These displacements may be used directly and/or indirectly (e.g., summations, averages, extrema magnitudes, RMS, or the like), perhaps to derive usable summary and point-by-point limb motion metrics.

The summary motion metrics may include, but are not limited to, angular range of motion (e.g., degrees) for swing and/or stance phases, duration (e.g., milliseconds) for the swing phase and stance sub-phases (e.g., landing, weight-bearing, and/or breakover), landing absorption (e.g., the average, peak, root mean square, and perhaps even the like of erratic, oscillatory limb motion in all directions (e.g., degrees/second)).

Additionally, differences between each of the angular displacement and angular velocity curves can be compared either for the same limb (unilateral) or between limbs (bilateral) on a point by point basis (perhaps for each data collection time point over the course of a stride). These differences can be averaged over multiple strides (aggregated across each run within a session for intra-session comparison or runs among sessions for multi-session comparison), and the results may be displayed, perhaps with animation and/or graphically, as an average difference curve (e.g., over the entire stride and/or for each stride phase or the like). These difference-curves can highlight non-uniform motion signatures and/or patterns that can be visualized and even recognized at a glance as indicative of the type and/or source of lameness.

Figure 8:
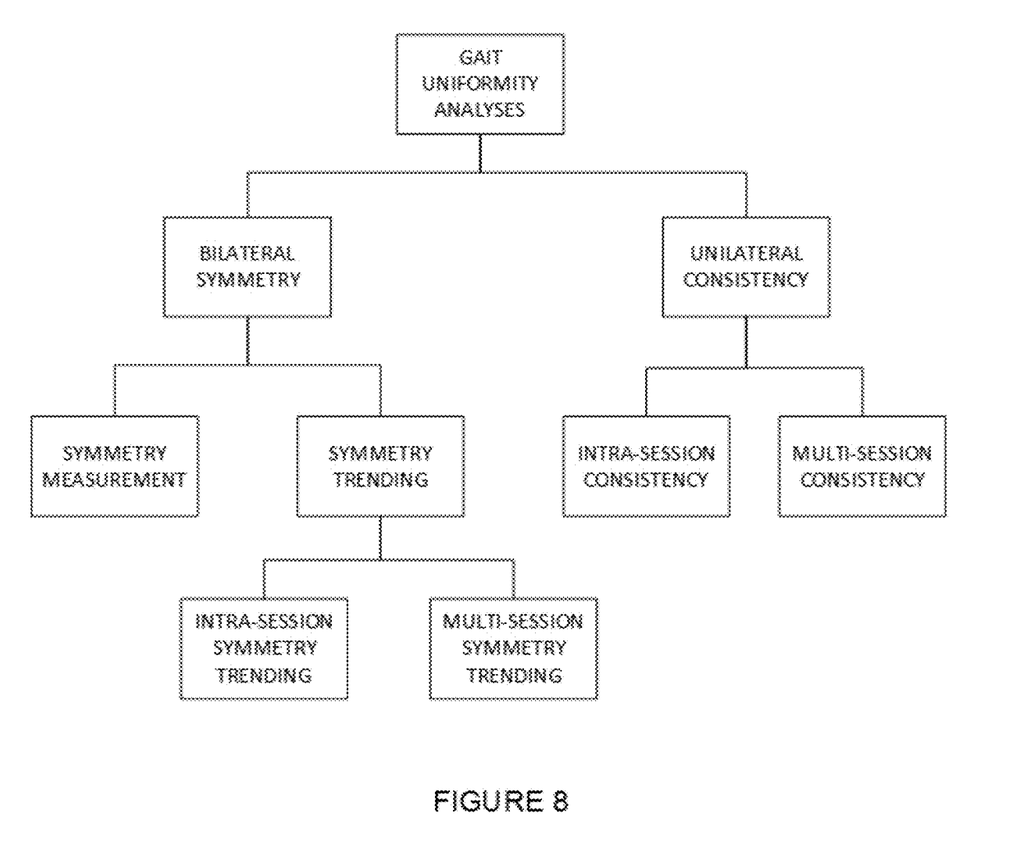
FIG. 8 shows a schematic diagram of the types of gait uniformity analyses (bilateral symmetry and unilateral consistency) and their subcategories (symmetry measurement, intra-session symmetry trending, multi-session symmetry trending, intra-session consistency and multi-session consistency) in accordance with various embodiments of the present invention.

Once derived, the summary motion metrics may be submitted for analyses 614. The goal of the uniformity analysis process may be to quantify the difference in the motion of one limb compared to itself (unilateral consistency) or to compare the difference between contralateral limbs (bilateral symmetry) (refer to FIG. 8). With both approaches, the horse may serve as their own reference for sensitive detection of limb motion that may be considered abnormal for that particular horse.

If the horse is run multiple times in order to immediately evaluate the effect of an intervention performed to improve the quality of the gait (e.g. nerve block, therapeutic shoeing/trim, or the like) or degrade the quality of the gait (e.g. joint flexion or the like) it may be decided to perform a unilateral consistency analysis to compare the change in motion of a single limb (intra-session consistency) or a bilateral trending analysis to compare the change in symmetry between left and right contralateral limbs (intra-session symmetry trending). These analysis approaches may also be performed to monitor the long term change in gait quality over weeks or months (e.g. lameness recovery, the effect of change in riding technique on gait quality, or the like) (multi-session consistency or symmetry trending). The unilateral consistency method may include random pairing of strides across the runs compared 616. The bilateral trending method may include pairing left and right strides, perhaps ensuring they occurred under comparable speeds and even conditions throughout the run 618.

It may also be decided to evaluate the bilateral symmetry of limb motion (e.g., the motion of the left forelimb versus the right forelimb) during a single run (symmetry measurement). This method may include pairing left and right strides

618. This analysis approach may provide immediate insight into the presence of lameness, the potential location, and perhaps even the severity of lameness. The typical methodology used to analyze the degree of uniformity 620 between two sets of measurements may be to compare the set of paired measurement differences using statistical inference based on averages and their associated confidence intervals (a.k.a. Limits of Agreement (LOA) or the like). For example, stride inertial measurement (SIM) values paired across left and right limb strides for the same run ($Left_{run1}$ vs. $Right_{run1}$) or paired strides collected from the same limb across two runs ($Left_{run1}$ vs. $Left_{run2}$). The uniformity (agreement) limits may be estimated with confidence intervals. Estimation of valid confidence intervals may rely on fulfilling several LOA analysis assumptions. Various transformations of the data may help fulfill these assumptions (e.g. the log transformation or the like may work well when the variance of the paired differences increases over larger average metric values, counteracting the normality assumption).

The reported limb motion findings may be designed to be quantified indicators of the level of motion uniformity (maybe as time-point bilateral symmetry between left and right limbs, as bilateral symmetry trending over time between left and right limbs, as unilateral consistency over time for a single limb, or otherwise). The uniformity findings may be made available for either a single leg, a pair of legs (e.g., front or hind) or even across all four limbs, as aggregated results may allow for a full gait assessment. Multiple motion metrics may be analyzed for uniformity, including, but not limited to, stride phase specific angular range of motion, duration, angular velocity or the like. The motion metrics may be displayed 622 on the mobile device (104) perhaps for immediate use or on a personal computer with a larger graphics display. The ability to assess uniformity across multiple motion parameters for a horse may assist with detection of the onset of subtle lameness or the effectiveness of a therapy as early as possible.

The limb motion findings may be managed and reported in a manner to support multiple types of uses 622. Easy to understand gait uniformity indices indicative of potential lameness may be reported in a manner meant to provide horse owners with ancillary evidence perhaps useful in deciding whether to call the veterinarian for diagnosis. Gait quality metrics (e.g., swing range of motion, stance/swing ratio, or the like) may be provided to support horse owners' monitoring gait improvements, perhaps in response to conditioning and/or application of specific training techniques. The various limb motion uniformity indices and values (e.g., lower limb angular range of motions, stride phase durations, or the like) may be provided with confidence intervals to inform the diagnosis and treatment of lameness by veterinarians in collaboration with other sources of evidence. A methodical lameness evaluation may be performed as a series of tests that are chosen based on interpretation from the overall impression, history, visual observations, and findings from diagnostic procedures (e.g., joint flexion, local anesthesia, or the like). Ancillary biosensing technology may be used for assisting with diagnosis and assessing the effectiveness of therapy. Trending and consistency across runs or time (over multiple sessions) may provide a way to immediately assess the response to a diagnostic procedure, monitor the progression of lameness, or perhaps to assess the efficacy of a treatment plan. Additionally, the raw stride inertial data values may be made available for transfer to facilitate further analysis and even sharing between practitioners and researchers.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in this or any subsequent patent application.

It should also be understood that a variety of changes may be made without departing from the essence of the invention. Such changes are also implicitly included in the description. They still fall within the scope of this invention. A broad disclosure encompassing the explicit embodiment(s) shown, the great variety of implicit alternative embodiments, and the broad methods or processes and the like are encompassed by this disclosure and may be relied upon when drafting the claims for this or any subsequent patent application. It should be understood that such language changes and broader or more detailed claiming may be accomplished at a later date (such as by any required deadline) or in the event the applicant subsequently seeks additional patent filing(s) based on this filing. With this understanding, the reader should be aware that this disclosure is to be understood to support this or any subsequently filed patent application that may seek examination of as broad a base of claims as deemed within the applicant's right, and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "biosensor" should be understood to encompass disclosure of the act of "biosensing"—whether explicitly discussed or not—and, conversely, were there effectively disclosure of the act of "biosensing", such a disclosure should be understood to encompass disclosure of a "biosensor" and even a "means for biosensing" Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms, such as contained in the Random House Webster's Unabridged Dictionary, second edition, hereby incorporated by reference. Finally, all references listed in the Information Disclosure Statement or any other information statement filed with the application are hereby appended and hereby incorporated by reference, however, as to each of the above, to the extent that such information or statements incorporated by reference might be considered inconsistent with the patenting of this/these invention(s), such statements are expressly not to be considered as made by the applicant(s).

Thus, the applicant(s) should be understood to have support to claim and make a statement of invention to at least: i) each of the biosensor devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

In addition and as to computer aspects and each aspect amenable to programming or other electronic automation, the applicant(s) should be understood to have support to claim and make a statement of invention to at least: xv) processes performed with the aid of or on a computer, machine, or computing machine as described throughout the above discussion, xvi) a programmable apparatus as described throughout the above discussion, xvii) a computer readable memory encoded with data to direct a computer comprising means or elements which function as described throughout the above discussion, xviii) a computer, machine, or computing machine configured as herein disclosed and described, xix) individual or combined subroutines and programs as herein disclosed and described, xx) a carrier medium carrying computer readable code for control of a computer to carry out separately each and every individual and combined method described herein or in any claim, xxi) a computer program to perform separately each and every individual and combined method disclosed, xxii) a computer program containing all and each combination of means for performing each and every individual and combined step disclosed, xxiii) a storage medium storing each computer program disclosed, xxiv) a signal carrying a computer program disclosed, xxv) the related methods disclosed and described, xxvi) similar, equivalent, and even implicit variations of each of these systems and methods, xxvii) those alternative designs which accomplish each of the functions shown as are disclosed and described, xxviii) those alternative designs and methods which accomplish each of the functions shown as are implicit to accomplish that which is disclosed and described, xxix) each feature, component, and step shown as separate and independent inventions, and xxx) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC*, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art should not be reasonably expected to have drafted a claim that would have literally encompassed such alternative embodiments.

Further, if or when used, the use of the transitional phrase "comprising" is used to maintain the "open-ended" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A system for monitoring gait in horses comprising:
   at least one sensor located in an equine conformal casing; wherein said equine conformal casing comprises a conformal curved interface on said conformal casing between said sensor and a leg of an equine, wherein said conformal curved interface is shaped to conform with and be in continuous external contact with an upper third metacarpal bone of said leg of said equine;
   a power source externally proximal to said equine conformal casing;
   a conformal casing fastener configured to fasten said equine conformal casing to said upper third metacarpal bone of said leg of said equine;
   at least one equine data transmitter located in said equine conformal casing; and
   an analytics module responsive to said at least one equine data transmitter;
   wherein said conformal curved interface is configured to couple said sensor to said upper third metacarpal bone of said leg of said equine,
   wherein said at least one equine data transmitter is configured to transmit raw data gathered by said sensor from said coupling of said sensor to said upper third metacarpal bone of said leg of said equine, and
   wherein said analytics module comprises an equine automatic stride phase segmenter being a software application designed to automatically segment equine run data from said raw data into an equine stance stride phase, an equine swing stride phase, and stride sub-phases.

2. The system of claim 1, further comprising at least one equine data processor.

3. The system of claim 1, wherein said equine conformal casing, said at least one sensor located in said equine conformal casing, and said conformal casing fastener are configured to detect equine motion.

4. The system of claim 3, wherein said equine conformal casing, said at least one sensor located in said equine conformal casing, and said conformal casing fastener are configured to minimize detection of inertia not associated specifically with equine strides.

5. The system of claim 4, wherein said equine conformal casing, said at least one sensor located in said equine conformal casing, and said conformal casing fastener are configured to be highly affixed to said upper third metacarpal bone of said leg of said equine.

6. The system of claim 3, wherein said equine conformal casing, said at least one sensor located in said equine conformal casing, and said conformal casing fastener are configured to minimize spurious motion.

7. The system of claim 1, wherein said analytics module is configured to process said raw data received from said at least one equine data transmitter.

8. The system of claim 7, wherein said analytics module is configured to process unfiltered data received from said at least one equine data transmitter.

9. The system of claim 1, wherein said power source externally proximal to said equine conformal casing is wired to said equine conformal casing.

10. The system of claim 1, wherein said stride sub-phases are selected from a group consisting of: an equine landing stride sub-phase, an equine weight-bearing equine stride sub-phase, an equine breakover stride sub-phase, an equine limb-raising stride sub-phase, an equine forward-rotation stride sub-phase, and an equine limb-lowering stride sub-phase.

11. The system of claim 1, wherein said stride sub-phases are selected from a group consisting of: an equine relatively high acceleration event sub-phase, an equine relatively high deceleration event sub-phase, an equine upward motion event sub-phase, an equine downward motion event sub-phase, an equine forward motion event sub-phase, an equine transitory motion event sub-phase, an equine sequential motion event sub-phase, and an equine sequential transitory motion event sub-phase.

* * * * *